(12) United States Patent
Ruech

(10) Patent No.: US 7,741,481 B2
(45) Date of Patent: Jun. 22, 2010

(54) METHOD FOR PRODUCING PURE MELAMINE

(75) Inventor: Wolfgang Ruech, Taiskirchen (AT)

(73) Assignee: AMI-Agrolinz Melamine International GmbH, Linz (AT)

( * ) Notice: Subject to any disclaimer, the term of this patent is extended or adjusted under 35 U.S.C. 154(b) by 736 days.

(21) Appl. No.: 11/547,573

(22) PCT Filed: Apr. 12, 2005

(86) PCT No.: PCT/EP2005/003994

§ 371 (c)(1),
(2), (4) Date: Oct. 3, 2006

(87) PCT Pub. No.: WO2005/100327

PCT Pub. Date: Oct. 27, 2005

(65) Prior Publication Data

US 2008/0275234 A1 Nov. 6, 2008

(30) Foreign Application Priority Data

Apr. 14, 2004 (DE) .................. 10 2004 018 784

(51) Int. Cl.
C07D 251/60 (2006.01)
C07D 251/62 (2006.01)
(52) U.S. Cl. ...................... 544/203; 544/201
(58) Field of Classification Search .................. 544/203, 544/201
See application file for complete search history.

(56) References Cited

U.S. PATENT DOCUMENTS

| 3,116,294 A | 12/1963 | Marullo et al. |
| 3,132,143 A | 5/1964 | Fogagnolo et al. |
| 5,721,363 A | 2/1998 | Canzi et al. |
| 6,790,956 B1 | 9/2004 | Coufal |
| 6,870,050 B2 | 3/2005 | Coufal et al. |
| 7,176,309 B2 * | 2/2007 | Schroder et al. ............ 544/203 |
| 2005/0119483 A1 | 6/2005 | Coufal |
| 2005/0131228 A1 | 6/2005 | Schroder et al. |

FOREIGN PATENT DOCUMENTS

| CA | 2350777 | 5/2001 |
| DE | 10229100 | 7/2003 |
| EP | 0799212 | 1/1999 |
| EP | 1345912 | 7/2004 |
| WO | 9620182 | 7/1996 |
| WO | 9623778 | 8/1996 |
| WO | 0029393 | 5/2000 |
| WO | WO 0146159 A2 * | 6/2001 |
| WO | 0212206 | 2/2002 |
| WO | 02051818 | 7/2002 |
| WO | 03045927 | 6/2003 |
| WO | 03053943 | 7/2003 |

* cited by examiner

Primary Examiner—Venkataraman Balasubramanian
(74) Attorney, Agent, or Firm—The Webb Law Firm

(57) ABSTRACT

The invention relates to a method for producing pure melamine by preparing a melamine melt, which is obtained in a high pressure process and from which the reaction gases are removed. Said method is characterized in that the melamine melt is quenched by water with a purity in excess of 95 wt. %, that $NH_3$ and $CO_2$ are subsequently removed from the obtained melamine solution and that alkali is added to said melamine solution and the mixture is then left to rest, whereby pure melamine is obtained by crystallization. Thus a melamine can be obtained with the same quality as that produced in known comparative methods, using smaller quantities of alkali.

19 Claims, 1 Drawing Sheet

METHOD FOR PRODUCING PURE MELAMINE

BACKGROUND OF THE INVENTION

1) Field of the Invention

The Application relates to a process for the preparation of pure melamine according to claim 1.

2) Description of the Related Art

In the high-pressure processes for the preparation of melamine, in general urea melt and optionally gaseous ammonia are reacted without the presence of a catalyst, for example at temperatures between 325 and 450° C., preferably between 350 and 425° C., and pressures between 50 and 250 bar to give liquid melamine and off gas. The reaction off gas mainly comprises ammonia and carbon dioxide, with small amounts of gaseous melamine. In addition to unconverted urea, the liquid crude melamine also contains byproducts, such as, for example, melem, melam and further condensation products of melamine, which are undesired in the end product and therefore have to be separated off. The melamine byproducts are separated from melamine by utilizing the known fact that the byproducts hydrolyze with water, preferably in the presence of alkalis, to give oxoaminotriazine compounds, such as ammeline and ammelide. During the subsequent melamine crystallization, these are kept in solution so that the pure melamine crystallizes out selectively. In these melamine processes, the melamine melt from the high pressure part is worked up in a downstream low pressure part in the presence of water.

According to U.S. Pat. No. 3,132,143, for example, the reaction mixture from the high pressure synthesis reactor, consisting of the melamine melt and the off gas, is fed to a quencher in which the mixture is brought into contact with an aqueous solution saturated with ammonia and carbon dioxide, at from 100 to 200° C. and from 10 to 35 bar for from 10 to 60 min. On contact with the cool quench solution, the melamine is absorbed therein while the major part of the off gas is separated off. For the degradation of the byproducts, the melamine solution is allowed to reside for from 20 to 50 min, the $NH_3$ and $CO_2$ contained is then removed with the aid of steam and, after addition of alkali-containing mother liquor and filtration of insoluble products, the melamine crystallizes out.

A disadvantage of this process is the fact that the melamine off gas is separated from the melamine only in the quencher and is thus obtained at a low pressure level and in a state which is not anhydrous. Since the off gas mainly comprises $NH_3$ and $CO_2$, considerable amounts of $CO_2$ are introduced into the wet part of the plant. $CO_2$ which has already been separated off is even recycled into the melamine process via the $CO_2$-containing quench liquid, with the result that the $CO_2$ content of the melamine solution is increased and hence the pH of the solution is reduced. This is disadvantageous in particular for the byproduct degradation preferably taking place in the alkaline range during the residence in the quencher, since this takes place slowly and incompletely under these conditions. The total $CO_2$ is stripped from the melamine solution only in the steam stripper of the wet part. This is also very energy-consumptive.

WO 00/29393 A1 or WO 03/045927 A1 describes melamine preparation processes in which the melamine melt is separated from the reaction off gas in the high pressure reactor itself. The off gas is obtained in anhydrous form and at high pressure and is recycled into the urea plant. The melamine melt fed for further working-up accordingly already contains a $CO_2$ content reduced by the proportion of off gas. Subsequently, the $CO_2$ dissolved in the melamine melt is removed from the melt, for example by passing through $NH_3$. The melamine melt pretreated in this manner is then fed to the quencher, in which the melamine melt is converted into a melamine suspension or solution by contact with an aqueous, alkali-containing solution. In order to accelerate the byproduct degradation and to keep oxoaminotriazine compounds formed thereby, ammeline and ammelide, in solution, NaOH is added to the melamine solution before it is allowed to reside for byproduct degradation. Dissolved $NH_3$ still present is then stripped out and the melamine finally crystallizes out. A disadvantage of these processes is the fact that considerable amounts of $CO_2$ are still present in the melamine suspension or solution discharged from the quencher. Said amounts arise because of incomplete $CO_2$ removal in the high pressure part and as a result of hydrolytic decomposition of unconverted urea and melamine byproducts in the quencher. The total $CO_2$ present must be neutralized by adding NaOH. Only on further addition of NaOH does the pH increase. A high pH is required for rapid byproduct degradation during the subsequent residence of the melamine solution. This results in very large amounts of NaOH for the desired high melamine purity with low byproduct contents, which amounts are undesired for economic and logistical reasons.

It was accordingly the object to provide a melamine process which has a reduced NaOH consumption in combination with the same energy characteristics of the plant and the same quality of the end product melamine.

SUMMARY OF THE INVENTION

According to the invention, this object is achieved by quenching the melamine melt with water having a purity of more than 95% by weight and by removing the $CO_2$ and $NH_3$, present in the melamine solution, before the addition of NaOH and before allowing residence for the byproduct degradation.

The present invention accordingly relates to a process for the preparation of pure melamine by working up a melamine melt obtained from a high pressure process and freed from the reaction off gases, in which a) the melamine melt is quenched with water having a purity of more than 95% by weight, b) $NH_3$ and $CO_2$ are then removed from the melamine solution obtained and c) alkali is then added to the melamine solution and said solution is then allowed to reside, d) whereupon pure melamine is obtained by crystallization.

According to the invention, the total $CO_2$, on the one hand entrained from the high pressure part and on the other hand formed in the quencher itself by hydrolysis, is removed from the melamine solution directly after the quenching with water having a purity of 95% by weight. Thus, alkali is subsequently added to a virtually $CO_2$-free melamine solution, which leads to an immediate pH increase in the melamine solution. Since a high pH is required for rapid byproduct degradation during the subsequent residence, the same melamine quality as in the known comparative processes is achieved in the process according to the invention with smaller amounts of alkali.

DETAILED DESCRIPTION OF THE PREFERRED EMBODIMENT

Figure 1:
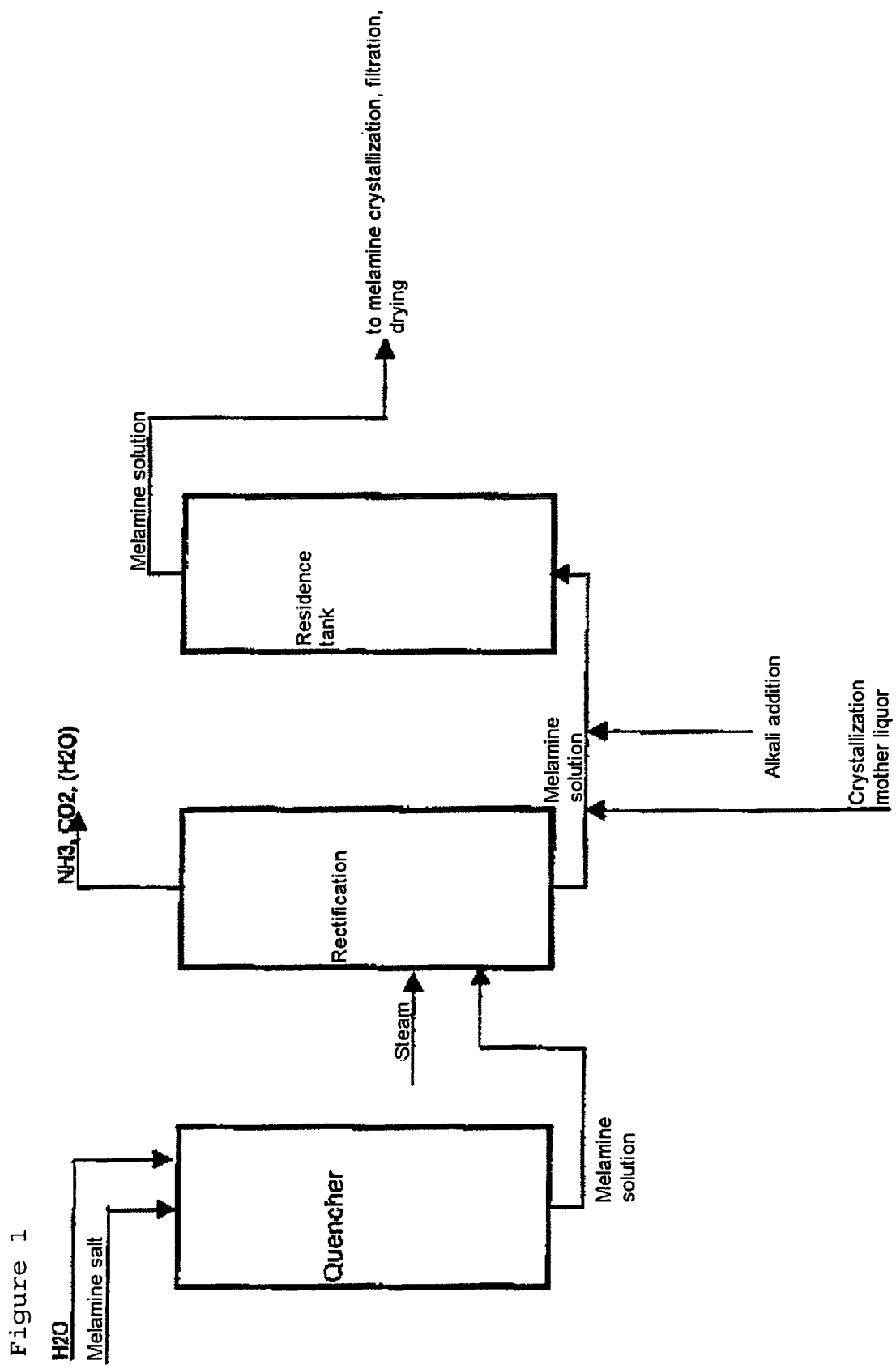
FIG. 1 is a block diagram of the process of the present invention.

In the present process, any melamine melt originating from a high pressure process can be used after the reaction off gases have been separated off. Particularly pure melamine is obtained if the melamine melt is prepurified before the quenching, in the high pressure part of the melamine plant. For example, it is possible partly to remove byproducts present in the melt by cooling and/or residence of the melamine melt under high-ammonia pressure. It is advantageous to use ammonia-saturated melamine melt in the present process.

In a preferred embodiment, the $CO_2$ dissolved in the melamine melt is substantially removed before the quenching. This is effected, for example, by treatment of the melamine melt with gaseous ammonia. In this way, only relatively small proportions of $CO_2$ have to be removed from the melamine solution in the wet part after the quenching, which is advantageous with respect to energy.

The melamine melt to be worked up according to the present process is fed to the quencher at a temperature of from about 330 to 400° C., preferably from about 330 to 380° C., particularly preferably from about 330 to 360° C., and a pressure of from about 50 to 600 bar, preferably from about 50 to 250 bar, particularly preferably from about 70 to 170 bar.

In the quencher, the quenching of the melamine melt is effected with water having a purity of more than 95% by weight, with the result that the melamine melt is converted into a melamine solution.

Advantageously used water is boiler feed water and/or condensed steam. It is furthermore possible to use the worked-up and purified waste water of the melamine plant for quenching the melamine melt in the quencher.

The quenching of the melamine melt is advantageously effected at from 170 to 220° C., particularly preferably at from 180 to 200° C. The increased temperature during quenching makes it possible to obtain a more highly concentrated melamine solution owing to the greater melamine solubility. This permits smaller apparatus volumes in the wet part and has energy advantages in the removal of $NH_3$ and $CO_2$ as a result of the recycling of small amounts of water. Unconverted urea or intermediates is or are hydrolyzed in the quencher to give $NH_3$ and $CO_2$. The exact temperature in the quencher can be established via the ratio of quench water to melamine melt and/or via the quench water temperature. The pressure in the quencher is, for example, the equilibrium pressure established at the respective temperature.

It is advantageous if the melamine solution obtained during the quenching has a melamine concentration of from 10 to 40% by weight, preferably from 20 to 30% by weight, particularly preferably 25% by weight. In this case, the ratio of quench water to melamine melt is about 3 t of quench water/t of melamine melt. $NH_3$ and $CO_2$ are then removed from the melamine solution discharged from the quencher. This is advantageously effected at virtually the same temperature as the quenching or at a higher temperature than the quenching. This ensures that the hydrolysis beginning in the quencher can be continued and the resulting $CO_2$ and $NH_3$ can be separated off immediately. The temperature is chosen to be so high that there is no danger with regard to crystallization of melamine during the removal of $NH_3$ and $CO_2$. After the $CO_2$ and $NH_3$ removal, a purified melamine solution having about the same melamine concentration as at the quencher discharge is obtained. For example, the melamine concentration is about 25% by weight and the temperature about 200° C.

It is advantageous if the removal of $NH_3$ and $CO_2$ from the melamine solution is effected in a rectification column, $NH_3$ and $CO_2$ being stripped from the melamine solution with steam and being recovered in the form of a liquid which is as concentrated as possible. This has the advantage that, when the recovered contents are recycled in a urea plant or into the liquid fertilizer area, the energy used in the respective plant is not adversely affected by an excessively great water supply. The recovery is effected, for example, as liquid $NH_3$ with up to about 20% by weight of $CO_2$ or as ammonium carbonate liquor or in the form of two fractions as ammonium carbonate liquor and as liquid $NH_3$.

Before the residence of the purified melamine solution for byproduct degradation, alkali is added to the melamine solution. The alkali used may be, for example, NaOH or KOH. NaOH, for example an aqueous NaOH solution having an NaOH concentration of about 50% by weight, is preferably used. The amount of alkali is from about 30 to 60 kg, preferably from 40 to 50 kg of 50% strength NaOH per t of melamine. The addition of alkali results in an increase in the pH, a pH between pH 9 and 12 being advantageous. A high pH is desirable for sufficiently rapid byproduct degradation.

Advantageously, the purified, virtually $NH_3$- and $CO_2$-free melamine solution, which has a melamine concentration of from about 10 to 4.0% by weight, preferably from 20 to 30% by weight, particularly preferably 25% by weight, is diluted to a melamine concentration of 5-20% by weight, preferably about 8% by weight, before the residence. Starting from 170 to 220° C., preferably from 180 to 200° C., the temperature of the melamine solution is reduced thereby to 120 to 200° C., preferably to 125 to 170° C., particularly preferably to 130° C. The dilution and cooling of the melamine solution result in a simple mode of operation for the subsequent melamine working-up steps.

It is advantageous if the dilution and cooling are effected by adding a solution containing recycled crystallization mother liquor. Since the crystallization mother liquor is alkali-containing, the fresh alkali supply can be reduced in this way. Moreover, the melamine yield of the plant increases as a result of the recycling and the amount of waste water to be worked up decreases.

It is possible to carry out the alkali addition and the addition of the dilution and cooling solution simultaneously. For example, alkali and dilution and cooling solution can be mixed and then fed together to the melamine solution. The advantage of thorough mixing and homogeneous distribution of the individual streams is achieved thereby. It is furthermore possible for the alkali addition and the addition of the dilution and cooling solution to be effected separately from one another in any desired sequence.

After the alkali addition, residence of the melamine solution is effected. Byproducts, such as, for example, melem and melam, are degraded thereby. The residence time is advantageously from 5 to 60, preferably from 20 to 40, min. In this way, the undesired melamine hydrolysis taking place simultaneously with the byproduct degradation can be kept low.

After the byproduct degradation, the melamine crystallizes out from the melamine solution, optionally after a pH adjustment. This is effected, for example, by temperature reduction and/or application of a vacuum. After subsequent filtration and drying, pure melamine is obtained.

The melamine obtainable by the present process has a purity of at least 99.8% and can be fed for any desired further processing.

EXAMPLE 1

NaOH Consumption in a Melamine Process According to the Prior Art

The crude melamine melt produced in the reactor is separated from the reaction off gases, and the melamine melt is then treated by passing through $NH_3$ and then introduced into a quencher. Since the melamine melt contains 1.5% by weight of $CO_2$, 15 kg of $CO_2$ per t of melamine melt are introduced into the quencher.

In the quencher, the melamine melt is brought into contact with NaOH-containing liquid. According to the equation

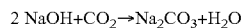

$$2\ NaOH + CO_2 \rightarrow Na_2CO_3 + H_2O$$

the NaOH reacts with the $CO_2$ present to give $Na_2CO_3$ and is therefore not available for the pH increase desired for the byproduct degradation.

Since 2 moles of NaOH are required per mole of $CO_2$, 54.5 kg of 50% strength NaOH are required per t of melamine melt from the synthesis part, simply for destroying the $CO_2$ introduced with the melamine melt into the quencher.

A further 45.5 kg of 50% strength NaOH/t of melamine melt are required for the byproduct degradation, i.e. the alkaline byproduct hydrolysis until the desired melamine purity is reached.

Accordingly, the resulting total NaOH consumption is 100 kg/t of melamine melt.

EXAMPLE 2

NaOH Consumption in the Process According to the Invention

A melamine melt which originates from a high pressure process and has been freed from the reaction off gases is treated with gaseous ammonia prior to quenching, in order to remove dissolved $CO_2$ substantially from the melamine melt. The melamine melt treated in this manner is fed to the quencher at a temperature of 350° C. and a pressure of 150 bar. The quenching is effected at 200° C. with boiler feed water. 3 t of quench water are added per t of melamine melt, which results in a melamine solution having a concentration of 25% by weight. $NH_3$ and $CO_2$ are then stripped from the melamine solution with steam at 200° C. The solution containing 25% by weight of melamine is diluted with recycled crystallization mother liquor to a melamine concentration of 8% by weight, the temperature of the solution being reduced to 130° C. 45.5 kg of 50% strength NaOH solution per t of melamine melt fed in are added for the byproduct degradation of the melamine solution, and the solution is allowed to reside for 30 min. The melamine is then crystallized out by temperature reduction, and the crystalline melamine is filtered and dried.

Since, in the process according to the invention, the NaOH is not fed in until after the complete removal of $CO_2$, the total amount of NaOH fed in is available only for the byproduct degradation. Accordingly, 54.5 kg of 50% strength NaOH, which are required in the comparative process for the $CO_2$ neutralization, are saved per t of melamine melt. In the melamine process according to the invention, an NaOH saving of at least half compared with a known comparative process is therefore achieved with the same melamine quality.

In FIG. 1, an embodiment of the process according to the invention is described by way of example.

The melamine melt which originates from a high pressure process and has been freed from the reaction off gases and was treated with gaseous ammonia prior to quenching is introduced into a quencher. $NH_3$ and $CO_2$ are then stripped from the melamine solution in a rectification column. The $NH_3$ and $CO_2$ stripped off are removed for further use. The melamine-containing solution is then diluted with crystallization mother liquor. An alkali-containing solution is added to the dilute melamine solution for byproduct degradation, and the solution is allowed to remain in a residence tank. The byproducts are then separated off and the melamine is crystallized out, filtered and dried.

The invention claimed is:

1. A process for the preparation of pure melamine by working up a melamine melt obtained from a high pressure process and freed from the reaction off gases, comprising the steps of:
   a) quenching the melamine melt with water having a purity of more than 95% by weight, whereby the quenching is effected at from 170 to 220° C.,
   b) removing $NH_3$ and $CO_2$ from the melamine solution obtained in step a), and
   c) adding alkali to the melamine solution and allowing said solution to reside,
   d) whereupon pure melamine is obtained by crystallization.

2. The process according to claim 1, wherein the water used is boiler feed water, condensed steam and/or the worked-up and purified waste water of the melamine plant.

3. The process according to claim 1, wherein the $CO_2$ dissolved in the melamine melt is removed therefrom prior to quenching.

4. The process according to claim 1, wherein the melamine solution obtained after the quenching has a melamine concentration of from 10 to 40% by weight.

5. The process according to claim 1, wherein the removal of $NH_3$ and $CO_2$ is effected at virtually the same temperature as the quenching or a higher temperature than the quenching.

6. The process according to claim 1, wherein the removal of $NH_3$ and $CO_2$ is effected in a rectification column, with $NH_3$ and $CO_2$ being stripped off with steam and recovered as concentrated liquid.

7. The process according to claim 1, wherein the recovery of $NH_3$ and $CO_2$ is effected as liquid $NH_3$ with up to about 20% by weight of $CO_2$ or as ammonium carbonate liquor or in the form of two fractions as ammonium carbonate liquor and as liquid $NH_3$.

8. The process according to claim 1, wherein the alkali used is NaOH.

9. The process according to claim 1, wherein the amount of alkali is from 30 to 60 kg of 50% strength NaOH per metric ton of melamine.

10. The process according to claim 1, wherein, prior to the residence in step c), the melamine solution is diluted to a melamine concentration of 5-20% by weight and cooled to a temperature of from 120 to 200° C.

11. The process according to claim 10, wherein the dilution and cooling are effected by adding a solution containing recycled crystallization mother liquor.

12. The process according to claim 11, wherein the residence is effected for from 5 to 60 min.

13. The process according to claim 1, wherein the quenching is effected at from 180 to 200° C.

14. The process according to claim 4, wherein the melamine solution obtained after the quenching has a melamine concentration of from 20 to 30% by weight.

15. The process according to claim 9, wherein the amount of alkali is from 40 to 50 kg of 50% strength NaOH per metric ton of melamine.

16. The process according to claim 10, wherein, prior to the residence in step c), the melamine solution is diluted to a melamine concentration of about 8% by weight.

17. The process according to claim 10, wherein, prior to the residence in step c), the melamine solution is cooled to a temperature of from 125 to 170° C.

18. The process according to claim 17, wherein, prior to the residence in step c), the melamine solution is cooled to a temperature of 130° C.

19. The process according to claim 12, wherein the residence is effected for from 20 to 40 min.

* * * * *